(12) United States Patent
Holjo et al.

(10) Patent No.: US 7,491,222 B2
(45) Date of Patent: Feb. 17, 2009

(54) COSMETIC TREATMENT APPARATUS

(75) Inventors: Ulf Peter Holjo, Tokyo (JP); Yoshiyo Wada, Yokohama (JP)

(73) Assignee: Scandinavia Corporation, Tokyo (JP)

( * ) Notice: Subject to any disclaimer, the term of this patent is extended or adjusted under 35 U.S.C. 154(b) by 565 days.

(21) Appl. No.: 10/897,184

(22) Filed: Jul. 21, 2004

(65) Prior Publication Data
US 2005/0245997 A1 Nov. 3, 2005

(30) Foreign Application Priority Data
Apr. 28, 2004 (JP) ............ P2004-133858

(51) Int. Cl.
*A61N 5/06* (2006.01)

(52) U.S. Cl. ............ 607/88; 607/90; 606/9; 606/10

(58) Field of Classification Search ............ 607/88–91, 607/94, 95; 606/3, 9–12
See application file for complete search history.

(56) References Cited

U.S. PATENT DOCUMENTS

| | | | |
|---|---|---|---|
| 5,444,310 A * | 8/1995 | Kataoka et al. ............ 307/125 |
| 5,683,380 A | 11/1997 | Eckhouse et al. |
| 5,720,772 A * | 2/1998 | Eckhouse ............ 607/88 |
| 5,757,140 A * | 5/1998 | Nilssen ............ 315/209 R |
| 6,094,595 A | 7/2000 | Takahashi |
| 6,632,218 B1 * | 10/2003 | Furumoto et al. ............ 606/9 |
| 2004/0147985 A1 * | 7/2004 | MacFarland et al. ............ 607/90 |
| 2006/0061299 A1 * | 3/2006 | Urakabe et al. ............ 315/291 |
| 2006/0074468 A1 * | 4/2006 | Neev ............ 607/90 |

FOREIGN PATENT DOCUMENTS

| | | |
|---|---|---|
| EP | 0596740 A1 | 11/1994 |
| GB | 2168554 A | 6/1986 |
| JP | 2892642 | 2/1999 |
| JP | 11-076434 | 3/1999 |
| JP | 2003-515959 | 5/2003 |
| JP | 2004-511315 | 4/2004 |
| WO | WO 01/41266 A1 | 6/2001 |
| WO | WO 02/32505 A1 | 4/2002 |

OTHER PUBLICATIONS

Patent Abstracts of Japan, No. 11-332951, Dec. 7, 1999, 1 p.
Patent Abstracts of Japan, No. 11-076434, Mar. 23, 1999, 1 p.
Patent Abstracts of Japan, Publication No. 11-223951, Dec. 7, 1999, 1 p.

* cited by examiner

*Primary Examiner*—Ahmed M Farah
(74) *Attorney, Agent, or Firm*—MacPherson Kwok Chen & Heid LLP

(57) ABSTRACT

A cosmetic treatment apparatus comprises a discharge lamp, a capacitor, and a current controller. The capacitor supplies an electric current for the discharge lamp. The current controller controls the electric current flowing from the capacitor to the discharge lamp. In a first stage of the cosmetic treatment, the current controller performs a constant current control operation. In this operation, the current flowing to the lamp does not vary with variations of the capacitor voltage. In the end stage of the treatment, the current is lower, and it decreases with the capacitor voltage.

16 Claims, 4 Drawing Sheets

COSMETIC TREATMENT APPARATUS

BACKGROUND OF THE INVENTION

1. Field of the Invention

The present invention relates to a cosmetic treatment apparatus. More particularly, the present invention relates to a cosmetic treatment apparatus for removing skin blemishes (i.e., blotches, freckles, wrinkles) and hair using a light beam.

2. Discussion of the Related Art

A cosmetic treatment apparatus using a light beam is disclosed in Japanese Patent No. 2892642. This device utilizes a halogen lamp and ozone produced by an electric discharge to effect cosmetic treatment such as removal of skin blemishes and hair.

SUMMARY OF THE INVENTION

It has been recently discovered that a cosmetic skin treatment of the kind described in the Japanese Patent No. 2892642 can also be performed by exposing a skin area to light emitted by a gas discharge lamp to locally heat the skin. A suitable cosmetic treatment apparatus includes a capacitor for a temporary storage of an electric energy sufficient to cause the desired heating.

The inventor has discovered however that the light emission in this device decreases over time because the current supplied by the capacitor decreases as the capacitor discharges. Consequently, the heating is not constant but changes over the course of the treatment. In many cases, constant heating is desired for application over a period of time. Due to the heat reduction during the course of the treatment, the heating may be insufficient near the end of the treatment even when a strong heat is applied at the beginning. The overall cosmetic treatment effectiveness is therefore reduced.

Some embodiments of the present invention provide a cosmetic treatment apparatus capable of emitting light at an intensity suitable for performing a cosmetic treatment over a period of time (an "irradiation period" of time).

In some embodiments, the capacitor discharge current is controlled by a current control device to provide a constant current control. The constant current control provides a sequence of identical pulses of current with an identical spacing between the pulses. It has been discovered that the constant current control stresses the current control device. Thus there is a need to reduce this stress to avoid the device failure. The inventor has discovered that the stress can be reduced without sacrificing the cosmetic treatment effectiveness if the constant current control is performed prior to an end stage of the irradiation period and the current is reduced in the end stage. The end stage current decreases with the capacitor voltage in some embodiments.

The features and advantages described above do not limit the invention. Other embodiments and variations are described below. The invention is defined by the appended claims which are incorporated into this summary section by reference.

DETAILED DESCRIPTION OF THE PREFERRED EMBODIMENTS

Figure 1:
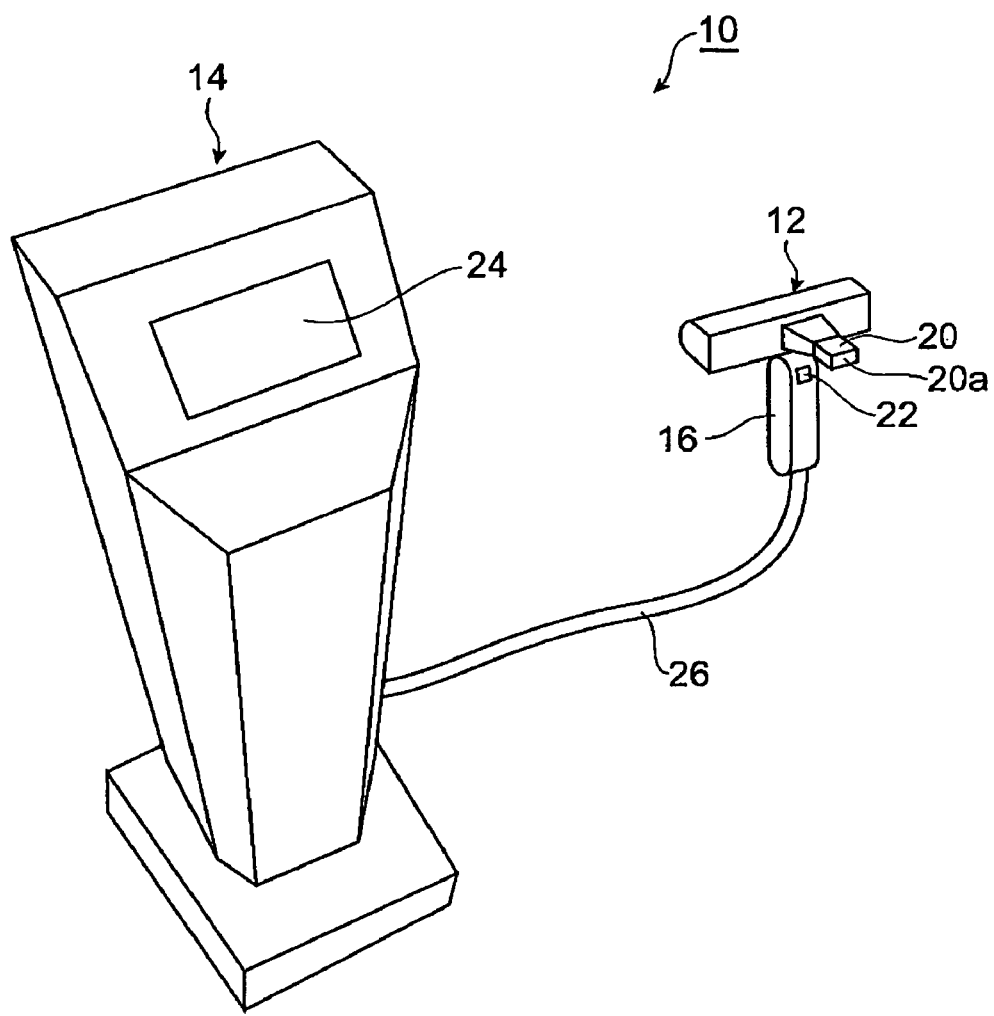
FIG. 1 is a general view of a cosmetic treatment apparatus according to an embodiment of the invention.

The preferred embodiments of the present invention are described below with reference to the accompanying drawings. In the drawings, the same elements are denoted by the same reference symbols. The drawings are not necessarily to scale, unless stated otherwise.

FIG. 1 shows a cosmetic treatment apparatus 10 according to an embodiment of the present invention. Apparatus 10 comprises a light emitting section 12 and a main controller 14. The light emitting section 12 includes a T-shaped operation handle 16 which incorporates a discharge lamp 18 (FIG. 2). e.g. as a Xe (xenon) lamp. Section 12 also includes a light guide 20 for guiding the light emitted by discharge lamp 18. The operation handle 16 is provided with a button 22. When an operator presses the button 22, the discharge lamp 18 is activated. The light generated by lamp 18 is conducted by light guide 20 and emitted from an exit surface 20a.

Main controller 14 contains a number of devices in its nearly rectangular-parallelepiped housing. A liquid-crystal display device 24 is provided in the upper part of main controller 14. Display device 24 can be a touch panel type for entry of treatment parameters.

Main controller 14 and light emitting section 12 are interconnected by a flexible cable 26. Light emitting section 12 can move freely over a treatment area.

Figure 2:
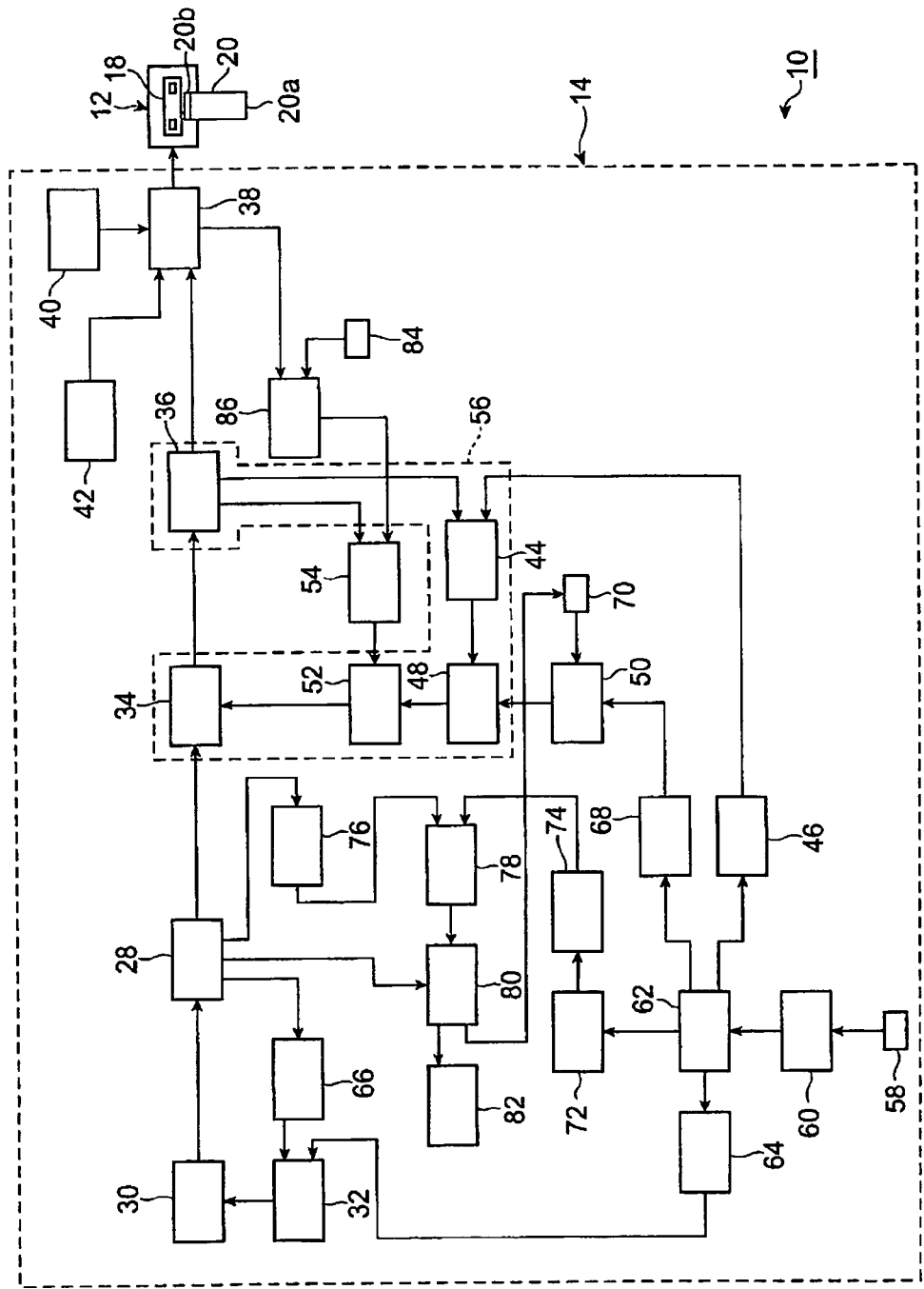
FIG. 2 is a block diagram showing some features of the cosmetic treatment apparatus of FIG. 1 in more detail.

FIG. 2 is a block diagram of cosmetic treatment apparatus 10 according to one embodiment. The discharge lamp 18 of the light emitting section 12 is shaped as a narrow tube. with a discharge length longer than the tube diameter. This lamp emits light at wavelengths of approximately 380 to 950 nm.

The light guide 20 is made from an optically transparent material and has a width approximately equal to the discharge length of the discharge lamp 18 and a thickness larger than the tube diameter. The light guide 20 has mirror-finished end faces. It receives and guides the light from the discharge lamp 18 through its entrance surface with a low loss. and emits the light from the exit surface 20a.

An optical filter 20b is provided at the entrance surface of the light guide 20. Filter 20b has a shape similar to the entrance surface of the light guide. The light emitted from the exit surface 20a has wavelengths of approximately 540 to 950 nm.

The exit surface 20a preferable has a large light emission area to avoid inefficient repetition of irradiation of large skin areas. In some embodiments, the exit surface 20a is 20 mm wide and 10 mm thick, In other embodiments, surface 20a is 35 mm wide and 10 mm thick. In some embodiments, surface 20a is 55 mm wide and 10 mm thick. Other dimensions are also possible. If light guide 20 is 20 mm wide, the light from lamp 18 should have a nearly uniform intensity per unit area over the width of 20 mm. Therefore, in some embodiments, the discharge lamp 18 has the discharge length nearly equal to the width of the light guide 20.

In some embodiments, the light guide 20 does not focus the light. This is done because the exit surface 20a is large while the discharge lamp 18 is made as small as possible to make the operation handle 16 sufficiently small to be held in a human hand. The discharge lamp 18 generates sufficient light energy to produce moderate heating of the skin without a light focusing action of the light guide 20.

The main controller 14 has a capacitor 28 for supplying an electric current for the discharge lamp 18. The capacitor 28 stores enough electric energy to cause a desired local heating in a treated skin area. The cosmetic treatment is performed during a single discharge of the capacitor 28.

A power supply 30 is connected to the capacitor 28. The power supply 30 receives an electric current from an ordinary alternating-current (AC) commercial distribution system and generates direct current (DC). The power supply 30 is controlled by a voltage control amplifier 32 described below. The power supply 30 charges the capacitor 28 to a desired preset voltage, and then cuts off the current to capacitor 28. The power supply 30 does not provide a current to the capacitor 28 when the capacitor voltage is greater or equal to the preset voltage.

A current control device 34, connected to the capacitor 28, controls an electric current flowing from the capacitor 28 to the discharge lamp 18. Current control device 34 can be a semiconductor device in which the current is controlled by a voltage. A power transistor, a MOSFET, an IGBT (insulated gate bipolar transistor), and other devices and circuits can be used. In one embodiment, device 34 is an IGBT serially connected between capacitor 28 and lamp 18. In the IGBT, the collector current controlled by the gate voltage remains constant even with an increase of the collector-emitter voltage. The collector current changes based on the gate voltage in the linear operation region. When the gate voltage increases further, the device enters the saturation region. This is a non-liner region, with the device acting as a turned-on switch. Cosmetic treatment apparatus 10 uses both the linear and the saturation modes of the current control device 34.

The output of current control device 34 is connected to a current detector 36 for detecting the electric current flowing to the discharge lamp 18. Current detector 36 can be, for example, a current transformer using a Hall element. Other detector types can also be used. Current detector 36 detects the electric current while being insulated from the current path to the discharge lamp 18. The current detector 36 is part of a negative feedback control system described below. Current detector 36 detects a pulsed current as described below, and has a wide operating range from DC to a high frequency to provide negative feedback control without sag.

The output of current detector 36 is connected to a trigger transformer 38 ("first circuit"). Trigger transformer 38 supplies a high-voltage trigger pulse to cause the discharge lamp 18 to emit light. In the present embodiment, the trigger transformer 38 is of a series type and is directly connected to the electrodes of the discharge lamp 18.

A trigger oscillator 40 is connected to the trigger transformer 38. The trigger oscillator 40 sends a signal to the trigger transformer 38 to generate a high-voltage trigger pulse for excitation of the discharge lamp 18. After the excitation of the discharge lamp 18, the trigger oscillator 40 automatically stops oscillating.

A microcurrent supply 42 is connected to the trigger transformer 38. Microcurrent supply 42 supplies a microcurrent to maintain a micro-emission in the discharge lamp 18 after the lamp excitation. The discharge lamp 18 is thus kept in the microemission state. Therefore, when a large electric current flows from the capacitor 28 into the discharge lamp 18 due to the operation of the current control device 34, the discharge lamp 18 is placed in a large emission state without a need for another trigger pulse.

A current control amplifier 44 compares the current detected by the current detector 36 with a preset current value established by a current setter 46 described below and outputs the amplified difference between the two values.

A feedback adjuster 48 receives a series of pulses from a pulse generator 50 and controls the current control device 34 to convert the current from the capacitor to a pulsed form. In this operation, the feedback adjuster 48 receives an output signal from the current control amplifier 44 and controls the current control device 34 so that the pulsed current flowing to the discharge lamp 18 corresponds to the preset value provided by the current setter 46.

A switch 52 is connected between the feedback adjuster 48 and the current control device 34. Switch 52 is an electronic switch. Switch 52 normally passes the output signal of the feedback adjuster 48 to the current control device 34, but when switch 52 receives a control signal from an error detection amplifier 54, switch 52 blocks the output signal of the feedback adjuster 48.

As described above, the current control device 34, current detector 36, current control amplifier 44, feedback adjuster 48, and switch 52 form a negative feedback current control system 56 ("current controller" 56) controlling the current from the capacitor 28 to the discharge lamp 18.

An input circuit 58 receives input values that define a desired light emission value to be obtained from the discharge lamp 18.

A processor 60 uses the light emission value in input circuit 58 to determine the corresponding current to the discharge lamp 18, the pulse waveform (the pulse width and the pulse spacing), and the pulsed emission time. The processor 60 also displays the light emission value provided by circuit 58 on the display device 24 (FIG. 1).

A first storage circuit 62 receives the parameters output by processor 60 and determines therefrom a charging voltage to be applied to the capacitor 28. First storage circuit 62 outputs a signal to drive a first voltage setter 64. The charging voltage for the capacitor 28 is determined to allow the current controller 56 to provide a constant current control (identical pulses) prior to the end stage of the irradiation and to provide a lower current, dependent on the capacitor voltage, in the end stage of the irradiation. The relationship between the parameters provided by processor 60 and the charging voltage is stored in advance in a storage device (not shown) within the first storage circuit 62. This relationship is based on the relationship between the discharge characteristics of the discharge lamp 18, the current to be provided to the discharge lamp 18, and the length of the irradiation period of time. The first storage circuit 62 determines the charging voltage from this relationship.

The first voltage setter 64 generates and outputs a reference value for the charging voltage to be applied to the capacitor 28. according to an output from the first storage circuit 62. As described above, processor 60, first storage circuit 62, and first voltage setter 64 form a charging voltage determining circuit for determining the charging voltage for the capacitor 28.

A first voltage detector 66 detects the capacitor voltage applied to the capacitor 28. The voltage detection incorporates a small delay. The first voltage detector 66 provides the capacitor voltage value to the voltage control amplifier 32. The voltage control amplifier 32 compares the capacitor voltage value received from the first voltage detector 66 with the reference value provided by the first voltage setter 64 and controls the power supply 30 to make the capacitor voltage equal to the reference value.

A pulse setter 68 receives a signal from the first storage circuit 62, sets a pulse width, a pulse spacing, and a pulse generation time, and provides a pulse emission signal to the pulse generator 50.

The pulse generator 50 generates a series of pulses corresponding to the pulse emission signal from the pulse setter 68.

A pulse enabling circuit 70 generates an output enable signal for pulse generator 50. When the signal is asserted, the pulses generated by pulse generator 50 are provided to feedback adjuster 48. The button 22 (FIG. 1) on operation handle 16 is electrically connected to pulse enabling circuit 70.

The current setter 46 receives a signal from the first storage circuit 62 and outputs a constant current reference value for discharge lamp 18. This reference value is fed to the current control amplifier 44.

A second storage circuit 72 includes a storage device (not shown). Second storage circuit 72 determines a maximum safe capacitor voltage for the capacitor 28. This is the maximum voltage considered safe for current control device 34. The voltage on capacitor 28 corresponds to the charging voltage determined by the first storage circuit 62. The current control device 34 provides the electrical current characteristics specified by pulse setter 68 and current setter 46, and accordingly is subjected to a stress because the current control device 34 is connected in series into the current path from the capacitor. The stress on the current control device 34 increases when the capacitor voltage increases, and the current control device 34 can fail if the stress exceeds a permissible amount. Second storage circuit 72 is provided to keep the stress on the current control device 34 within the permissible range.

The storage device (not shown) within the second storage circuit 72 stores the permissible stress amount for the current control device 34. Second storage circuit 72 determines the maximum safe capacitor voltage considered safe for the current control device 34, based on the charging voltage determined by the first storage circuit 62 and the permissible stress amount, and outputs a signal to drive a second voltage setter 74.

The second voltage setter 74 outputs the maximum safe capacitor voltage as a reference voltage, in accordance with the signal from the second storage circuit 72. As described above, processor 60, first storage circuit 62, second storage circuit 72, and second voltage setter 74 form a maximum safe capacitor voltage determining circuit for the capacitor 28.

A second voltage detector (capacitor voltage detecting circuit) 76 detects the voltage on capacitor 28. Second voltage detector 76 performs broadband noise filtering of the capacitor voltage.

An error detection amplifier 78 compares the capacitor voltage obtained from the second voltage detector 76 with the maximum safe capacitor voltage obtained from the second voltage setter 74 and activates a switch 80 to connect a load resistor 82 to the capacitor 28 if the capacitor voltage exceeds the maximum safe capacitor voltage. Load resistor 82 is provided for discharging the capacitor 28 when the capacitor is overcharged. The capacitor 28 is discharged until the capacitor voltage becomes smaller than the maximum safe capacitor voltage.

The switch 80 receives an output signal from the error detection amplifier 78, and controls the discharge of the capacitor 28 by connecting the capacitor 28 to the load resistor 82 or disconnecting the load resistor 82 from the capacitor 28. During the discharge of the capacitor 28 through the load resistor 82, the switch 80 controls the pulse enabling circuit 70 to block the light emission of the discharge lamp 18, overriding other inputs to pulse enabling circuit 70.

As described above, the error detection amplifier 78, switch 80, and load resistor 82 form a voltage reduction circuit for reducing the capacitor voltage to a value below the maximum safe capacitor voltage.

A reference voltage generator 84 provides a reference voltage for comparison with the lamp voltage applied to the discharge lamp 18. This reference voltage is lower than the lamp voltage induced by the current flowing from the microcurrent supply 42 to the discharge lamp 18.

A voltage comparator (determining means) 86 compares the lamp voltage applied by the trigger transformer 38 to the discharge lamp 18, with the reference voltage from the reference voltage generator 84. The voltage comparator 86 does not provide an output signal when the lamp voltage is above the reference voltage. When the lamp voltage is lower than the reference voltage, the voltage comparator 86 determines that the discharge lamp 18 is unable to emit light, and outputs a signal to the error detection amplifier 54.

The error detection amplifier 54 outputs a logical sum of two error detection signals for switch 52. One of the two error detection signals is asserted in response to a signal from the voltage comparator 86 to prevent the signal from the feedback adjuster 48 from being transmitted to the current control device 34. The other error detection signal is asserted by the current detector 36 when the current detector 36 detects an excessive current from the current control device 34. The output signal of error detection amplifier 54 is asserted when either one or both of the two error detection signals are asserted. When the output signal of error detection amplifier 54 is asserted, the switch 52 blocks the signal from the feedback adjuster 48 from being transferred to the current control device 34.

Now the control of the cosmetic treatment apparatus 10 will be described, prior to the description of the operation of the cosmetic treatment apparatus 10 according to one embodiment.

Let us suppose first that the current controller 56 is absent, and the current from the capacitor 28 is directly supplied to the discharge lamp 18. In this case, the capacitor voltage decreases as the capacitor discharges. The current flowing into the discharge lamp 18 and the lamp voltage are large in the early stage of the irradiation period. The current and the voltage decrease with time, and they decrease quickly in the end stage of the irradiation. Accordingly, the light emission from the discharge lamp 18 is large in the early stage of the irradiation period, decreases with time, and quickly decreases in the end stage of the irradiation.

Figure 3:
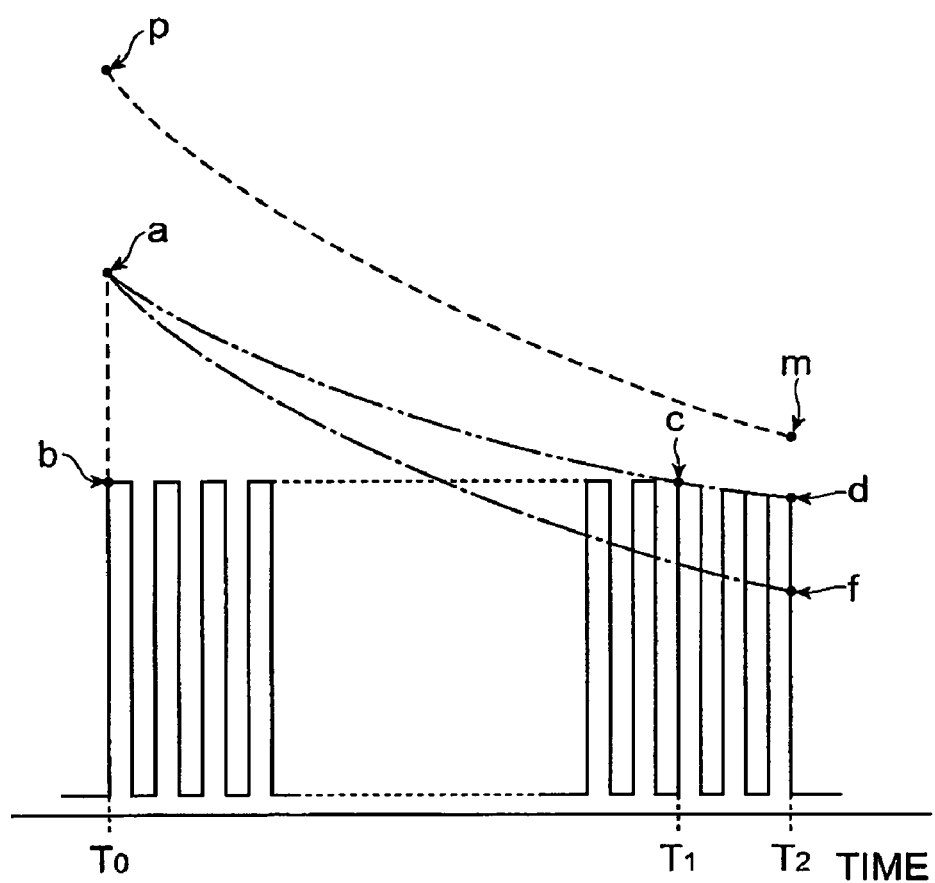
FIGS. 3 and 4 are graphs of electrical characteristics in one embodiment of the present invention.

Referring to FIG. 3, the capacitor voltage decreases during the discharge, and thus the lamp voltage decreases with time as indicated by an envelope curve af. Therefore, the emission in the early stage of the irradiation period is different from the emission in the end stage of the irradiation. As a consequence, the heat applied to the skin is not constant, and is too low in the end stage of the irradiation, thus reducing the effect of the cosmetic treatment.

In the cosmetic treatment apparatus 10 of the present embodiment, the current controller 56 controls the pulsed current flowing to the discharge lamp 18 so that the pulses remain constant prior to the end stage of the irradiation period (a multi-pulse emission period), and in the end stage of the irradiation period the pulsed current is lower and is a function of the capacitor voltage. This permits a substantially uniform heat application to the skin over the irradiation period.

More particularly, as shown in FIG. 3, in one irradiation period from a time T0 to a time T2, the current pulses provided to the discharge lamp 18 remain constant from the time T0 to a time T1. The time from T0 to T1 will be called a "constant current control section" herein. At time T0, the lamp voltage is shown as "b", though the capacitor voltage is "a". The voltage difference between a and b is the voltage appearing across the current control device 34 connected in series with the lamp. The product of this voltage, the current through current control device 34, and the current flow time is the stress on the current control device 34.

The capacitor voltage decreases with time, to a value "c" at time T1. The lamp voltage is also near c at time T1. Therefore, the collector-emitter voltage of the current control device 34 is small at time T1, and the device 34 is in saturation, acting essentially is a turned-on switch. After time T1, in the end stage from T1 to T2, the current flowing to lamp 18 is a function of the capacitor voltage and is lower than the current in the constant current control section [T0, T1]. Consequently, the lamp voltage decreases while remaining about equal to the capacitor voltage, as indicated by an envelope curve cd.

The points b, c, and d were described in terms of voltages, but they can also be described in terms of the current values, because the current increases with the lamp voltage. The reason why the voltage at point f is smaller than that at point d, as indicated in FIG. 3, is that in the early stage [T0, T1] the current is greater for the curve af, providing a greater capacitor discharge.

The area defined by the points a, b, and c indicates the stress on the current control device 34. This stress is determined as a sum of terms, each term being the product of (i) the difference between the ac curve value and the lamp voltage at the point b, (ii) the current at the point b, and (iii) the duration of a single pulse. Each of these products is computed for one pulse, and the products are summed over all the pulses between the time T0 and the time T1. If the stress on the current control device 34 is larger than a maximum rating of the device (which can be defined, for example, as a maximum load amount corresponding to a maximum collector load), the current control device 34 may fail.

For continuously applying constant heat to the skin throughout the entire irradiation period, it is preferable to set the capacitor voltage higher at the time T0 and perform the "constant current control" operation over the entire irradiation period, as indicated by an envelope curve pm in FIG. 3. However, this will increase the stress on the current control device 34 and the likelihood of damaging the current control device 34.

The inventor has determined that the heat application in the cosmetic treatment should preferably be performed in the form of multiple short pulses of about equal amounts of emission. However, the emission amounts do not have to be perfectly identical, and the treatment effect is not degraded at all if the emission is a little lower in the end irradiation stage.

Therefore, the cosmetic treatment apparatus 10 according to the present embodiment provides a lower electric current to the discharge lamp 18 in the end stage, whereby the capacitor voltage at the time T0 can be decreased to reduce the stress on the current control device 34 and reduce the possibility of damaging the current control device 34 while a suitable cosmetic treatment is provided.

If the point c is close to the point b, the voltage at the point a can be decreased, and the area defined by the points a, b, and c will be reduced, so as to reduce the stress on the current control device 34. However, the closer the point c to the point b, the shorter is the constant current control section, and hence the smaller is the total emission applied to the skin. Therefore, the point c is determined taking into account the stress on the current control device 34 and the emission needed for the treatment. The point c defines the time T1. In one embodiment, the ratio of the time (T2-T1) to the irradiation time (T2-T0) is at most 0.4. The period from the time T1 to the time T2 is called the "end stage of the irradiation." When the end stage duration is defined as described above. there is no substantial degradation of the cosmetic treatment despite the reduced emission. Typically, the irradiation period is approximately 4 msec to 80 msec. If, for example, the irradiation period is 60 msec, the end stage should not be longer than 24 msec.

If the irradiation time (T2-T0) is short, the area abc in FIG. 3 becomes small, the stress on the current control device 34 is reduced, and the ratio of the end stage duration (T2-T1) to (T2-T0) can be made small. On the other hand, if the irradiation period (T2-T0) is long, the area abc in FIG. 3 becomes large, the stress on the current control device 34 is large, and thus the ratio of the end stage duration (T2-T1) to (T2-T0) has to be large. The time T1 is generally set to provide a small ratio for a short irradiation period and a large ratio for a long irradiation period. T1 is thus set to keep the stress low on the current control device 34, while achieving an effective treatment.

If the irradiation period (T2-T0) is long, the treatment will not be degraded even if the emission per pulse is reduced near the end stage. Conversely, if the irradiation period (T2-T0) is short, the number of pulses is also reduced, and thus the emission per pulse may significantly affect the treatment. In this case, it may be desirable to keep the emission per pulse at a constant level throughout the treatment to achieve the highest treatment effect.

Now the overall operation of the cosmetic treatment apparatus 10 according to the present embodiment will be described.

First, the power is turned on to the cosmetic treatment apparatus 10. The trigger oscillator 40 applies a pulsed current to the primary winding of the trigger transformer 38 to generate a high-voltage pulse, of about 12 kV-20 kV, in the secondary winding. The trigger transformer 38 applies this pulse to the discharge lamp 18. This pulse excites the discharge lamp 18.

The microcurrent supply 42 has a high internal impedance. Before the excitation of the discharge lamp 18, microcurrent supply 42 outputs a high voltage to help discharge the lamp after a streamer has been produced in the lamp during the excitation. The discharge occurs immediately after the excitation. and the lamp impedance drops. The output voltage of microcurrent supply 42 decreases as the lamp impedance drops, due to the high internal impedance of circuit 42. Circuit 42 continues to supply enough current to maintain a weak emission discharge in the discharge lamp 18.

Due to this continuous week emission, a large current will flow without re-excitation if the voltage applied to the discharge lamp 18 is increased, and a large emission will occur without a new trigger pulse. When the discharge lamp enters the week emission state, the trigger oscillator 40 stops oscillating.

Next, the operator uses touch-panel device 24 (FIG. 1) to enter desired emission-related values for the skin treatment. These values are provided to the input circuit 58. As described above, the display device 24 is a touch panel type with a liquid crystal display. The display screen can be provided with windows corresponding to respective functions, and the operator touches the windows to select a function and enter a desired value.

For example, cosmetic content item windows may be provided such as skin blotches, wrinkles, sagging skin, and hair removal, and the operator selects a window corresponding to the desired treatment for entry of corresponding parameters. Different pulse waveforms can be defined in this way.

Furthermore, skin color differs among the individuals, and hence the light reflectance of the skin may differ from one person to the next. Therefore, the light reflectance should be taken into account in determining the emission. Hence, the emission-related values can be defined using the following technique. A color reference value is defined as 0 for the ordinary skin color. The color reference value is defined as +5 for the skin much whiter than the ordinary color, to indicate a larger skin reflectance. The color reference value is defined as −5 to indicate a much lower light reflectance relative the ordinary color. The intermediate values between −5 to +5 indicate the intermediate skin colors and define the electric current values for the discharge lamp 18. +5 corresponds to the maximum current, and −5 to the minimum current. Other numerical coding can also be used. For example, one can define the emission-related values in $J/cm^2$.

A display window can also be present for inputting a value for the hair color or hair thickness. In this case, there is no need for directly expressing the hair color or thickness as they can be represented by other related values. For example, in one embodiment, number 0 represents the ordinary hair thickness, +5 represents thin hair, and −5 represents thick hair. Intermediate numbers represent intermediate hair thickness. The hair thickness value corresponds to the number of pulses provided to the discharge lamp 18. In this example, +5 corresponds to the maximum number of pulses, and −5 to the minimum number of pulses.

These input values are provided to processor 60, and are used to define the emission of the discharge lamp 18.

The above-described display device 24 can be controlled by a programmable controller programmed to perform the functions described above. Other device types can also be used. For example, a non-touch-panel display can be used in conjunction with a keyboard. A personal computer can also be used to enter the parameters to apparatus 10.

The processor 60 receives digital signals identifying the input values. These signals are provided by the input circuit 58. Processor 60 outputs parameters to define the desired emission amount in accordance with the conditions stored in the storage device. These conditions define the appropriate values for the cosmetic content inputs entered into the display device 24 to obtain the appropriate pulse waveforms. The current to the discharge lamp 18 depends upon the numerical levels corresponding to the optical skin reflectance. The emission of the discharge lamp 18 depends upon the pulse waveform, the number of pulses, the pulse width, and the pulse current, and the skin heating can be different even for the same emission energy depending on whether the emission energy is applied instantaneously or spread over a long period of time.

Therefore, the current provided to the discharge lamp 18. the pulse waveform. the number of pulses, the pulse width, and the pulse spacing should be determined taking into account the cosmetic purposes, the skin reflectance, and the hair thickness. The first storage circuit 62 takes into account the mutually related values defining the current magnitude, the pulse waveform, the number of pulses, the pulse width, and the pulse spacing, which correspond to the conditions stored in advance in the storage device. For example, to provide a given emission energy, the current can be reduced if the number of pulses increases, whereas the current should be increased when the number of pulses decreases. The pulse spacing selection also necessitates changes of other parameters if the total emission energy is to be unchanged. Since the cosmetic treatment effects depend on these parameters, the signal generated by the first storage circuit 62 to define these parameters will be optimized for each cosmetic purpose, as defined by the storage device.

The circuitry of main controller 14 is preferably implemented as a software programmable controller (program controller). The controller may be specifically designed for the purpose. Alternatively, a logic circuit with a CPU can be used. A personal computer can also be used with a software to implement the storage and other functions.

The first storage circuit 62 determines the charging voltage to be applied to the capacitor 28, based on the above parameters received from the processor 60, and outputs a digital signal to drive the first voltage setter 64. The charging voltage to be applied to the capacitor 28 is determined with reference to the relationship between the above parameters and the charging voltages. The relationship is stored in advance in the storage device of the first storage circuit 62. The charging voltage determined at this point corresponds to the point a in FIG. 3, the current controller 56 will operate to provide the current as defined by the points b, c, and d.

When a large lamp current is desired, the voltage applied to the discharge lamp 18 is high and the voltage value at the point b is high; therefore, the charging voltage for the capacitor 28 corresponding to the point a is set to be high. Conversely, for a small lamp current, the voltage applied to the discharge lamp 18 is low and the voltage value at the point b is low; therefore, the charging voltage for the capacitor 28 corresponding to the point a is set to be low. In this manner, the charging voltage for the capacitor 28 corresponding to the point a is set to allow the current controller 56 to provide the current curve defined by the points b, c, and d.

The first voltage setter 64 generates a digital signal identifying the reference value for obtaining the charging voltage determined by the first storage circuit 62, converts the digital signal to an analog signal, and holds the analog signal. The first voltage setter 64 provides the analog signal to the voltage control amplifier 32. The first voltage detector 66 detects the voltage on the capacitor 28, and outputs the detected capacitor voltage to the voltage control amplifier 32. The voltage control amplifier 32 controls the power supply 30 so that the capacitor voltage is equal to the reference value. This causes the power supply 30 to charge the capacitor 28 to an adequate voltage to allow the current controller 56 to provide the current curve defined by the points b, c, and d.

The pulse setter 68 sets the pulse waveform, the pulse width, the pulse spacing, and the pulsed emission time (the irradiation period), based on the signal from the first storage circuit 62. The pulse generator 50 generates a desired series of pulses based on the signal from the pulse setter 68.

Based on the digital signal from the first storage circuit 62, the current setter 46 generates a digital signal representing the constant current to be delivered in each pulse to the discharge lamp 18, converts the constant current digital signal, to an analog signal, and holds the analog signal. The current setter 46 outputs the analog signal to the current control amplifier 44.

When the capacitor 28 has been charged up, the operator manipulates the operation handle 16 to position the light emitting section 12 so that the exit surface 20a of the light guide 20 contacts the skin treatment area. In order to moderately heat the skin with light emitted from the light guide 20, it is desirable to provide a substantially uniform light intensity distribution over the exit surface 20a of the light guide 20, and the exit surface 20a should be at a uniform distance from the skin surface and not at a large angle to the skin surface. In actual use, therefore, the treated area is coated with a transparent cream and the light guide 20 is pressed on top. This ensures a smooth contact between the light guide 20 and the skin surface, and provides a uniform light intensity over the treatment area of the skin.

When the operator presses the button 22 on the operation handle 16 to cause the pulse enabling circuit 70 to generate the output enable signal for the pulse generator 50, the pulse generator 50 provides a series of pulses to the feedback adjuster 48.

The current detector 36 detects the current flowing to the discharge lamp 18, and provides the current value to the current control amplifier 44. The current control amplifier 44 compares the current value provided by the current detector 36, with the preset value in the current setter 46, amplifies the difference between the two values, and outputs the amplified difference.

The feedback adjuster 48 receives the pulse series provided by the pulse generator 50, and controls the current control device 34 to convert the current to the device 34 to a pulsed form. In this operation, the feedback adjuster 48 receives the output signal from the current control amplifier 44 and controls the current control device 34 so that the pulsed current flowing to the discharge lamp 18 corresponds to the preset value provided by the current setter 46.

As a result, the current flowing from the capacitor 28 via the current control device 34 to the discharge lamp 18 has a desired value and causes the discharge lamp 18 to emit pulsed light. The short pulses of light repeatedly irradiate the treated part of skin in contact with the exit surface 20a of the light guide 20. This short pulse irradiation reduces diffusion of heat to areas adjacent to the skin treatment area and provides an effective warming of the treated area. In contrast, if the treated area were continuously exposed to a non-pulsed light, the treated area would be locally heated but the heat would gradually diffuse to the adjacent area so as to lower the temperature at the treated area. For cosmetic purposes it is desirable to warm only the treated area, and the heat diffusion will reduce the warming effect for the treated area. Use of very short light pulses will increase the warming effect.

In one example, an effective warming for the cosmetic treatment is achieved when about six to fifteen pulses of light are generated of 2 msec each at 2 msec intervals. To perform hair removal for cosmetic purposes, the emission of about 12-30 J/cm$^2$ is preferable. For removal of skin blotches, freckles, or wrinkles, the emission should be about 10-25 J/cm$^2$.

In this treatment, the light penetrates the skin while being attenuated by the surface layer, and the light reaches deep underneath the skin, as needed to achieve the desired cosmetic effect on the skin.

If there is a need to heat a relatively large area with a large instantaneous emission, the electric charge and the current provided to the discharge lamp 18 are large. For example, if the aforementioned skin color reference value is 0, the current of about 300 A is provided to the discharge lamp 18.

The emission from the discharge lamp 18 is defined by the current through the discharge lamp 18, the voltage, and the emission time. The lamp current varies with the voltage applied to the discharge lamp 18, increasing with the lamp voltage.

As the capacitor 28 discharges, the capacitor voltage decreases. See FIG. 3. The discharge current also decreases. During the time from T0 to time T1, the discharge lamp 18 emits light based on the current value determined by the current setter 46, with the voltage corresponding to this current value being applied to the discharge lamp 18.

When the capacitor voltage is larger than the sum of the lamp voltage and the collector-emitter saturation voltage of the current control device 34, the current control device 34 is in a linear region and the current control device 34 does not allow its output current to exceed the preset current value. This is the "constant current control" operation for the current flowing to the discharge lamp 18 during the time from T0 to T1, and pulses of light of equal emission energies are repeatedly provided to the treated area.

At the time T1, the current control device 34 becomes saturated due to its collector-emitter voltage value. At this time, the capacitor voltage is the sum of the lamp voltage and the collector-emitter voltage. The saturation value of the collector-emitter voltage depends on the device but is approximately 2 V.

As the capacitor 28 continues to discharge, the capacitor voltage decreases. However, since the current control device 34 is already saturated at the time T1, the negative feedback control system 56 does not provide a linear control even though the signal from the current setter 46 is provided to the current control amplifier 44. Therefore, the current control device 34 acts as a turned-on switch, and directly passes the current from the capacitor 28 to the discharge lamp 18. Therefore, in the end stage of the irradiation (from the time T1 to the time T2), the output current of current control device 34 varies according to the capacitor voltage, and the output current is lower than in the constant current control section. Consequently, as shown in FIG. 3, the voltage applied to the discharge lamp 18 decreases, and the light emission is lower. However, the cosmetic effect is not substantially affected by some decrease of the emission energy in the end stage of the irradiation, as described above.

The stress on the current control device 34 in one irradiation period is represented by the area defined by the points a, b, and c. as described above and shown in FIG. 3. The stress is lower in comparison with the case of the constant current control operation throughout the irradiation period (corresponding to the curve pm in FIG. 3), and hence the current control device 34 is less likely to fail.

Since the cosmetic treatment apparatus 10 according to the present embodiment is constructed so that the current controller 56 performs the constant current control prior to the end stage of the irradiation and passes a lower current, having a value depending on the capacitor voltage, to the discharge lamp 18 in the end stage of the irradiation,. it is feasible to provide a continuous stream of pulses at an intensity suitable for the cosmetic treatment while reducing the stress on the current control device 34 of the current controller 56. As a result, it becomes feasible to achieve the optimal cosmetic effect.

Since the stress on the current control device 34 can be reduced as described above, it becomes feasible to use an inexpensive device with a lower permissible load amount and thereby reduce the cost. Furthermore, less heat is generated by the current control device 34, and thus a smaller cooling mechanism needs to be provided, so that the size of the cosmetic treatment apparatus 10 can be reduced.

The power supply 30 charges the capacitor 28 over a period of time with a lower current than the discharge current flowing from the capacitor in a quick discharge. The power supply thus has a high internal impedance. Hence, the power supply 30 cannot supply a sufficient power to compensate for the diminishing lamp voltage and current during the irradiation period. After the irradiation period, the current controller 56 turns off the current supply to stop the current flow to the discharge lamp 18, and then the power supply 30 charges the capacitor 28 to the preset voltage.

Sometimes there is a need to change the emission energy during treatment. In this case, the operator enters new input values via the input circuit 58, whereupon the processor 60 generates new preset values for charging the capacitor 28. The new settings change the electric current flowing to the discharge lamp 18, the pulse waveform, the number of pulses, the pulse width, and the pulse spacing, according to changes of the parameters such as the cosmetic purpose. the skin reflectance, and the hair thickness. In accordance with the new parameters, the processor 60, the first storage circuit 62, and the first voltage setter 64 determine the new preset voltage value for the capacitor 28.

If the new preset voltage is much higher than the actual capacitor voltage at the time, the permissible load amount on the current control device 34 can be exceeded and the device can fail. Therefore, it is necessary to lower the capacitor voltage before continuing the lamp 18 operation. This will be described with reference to FIG. 4.

Figure 4:
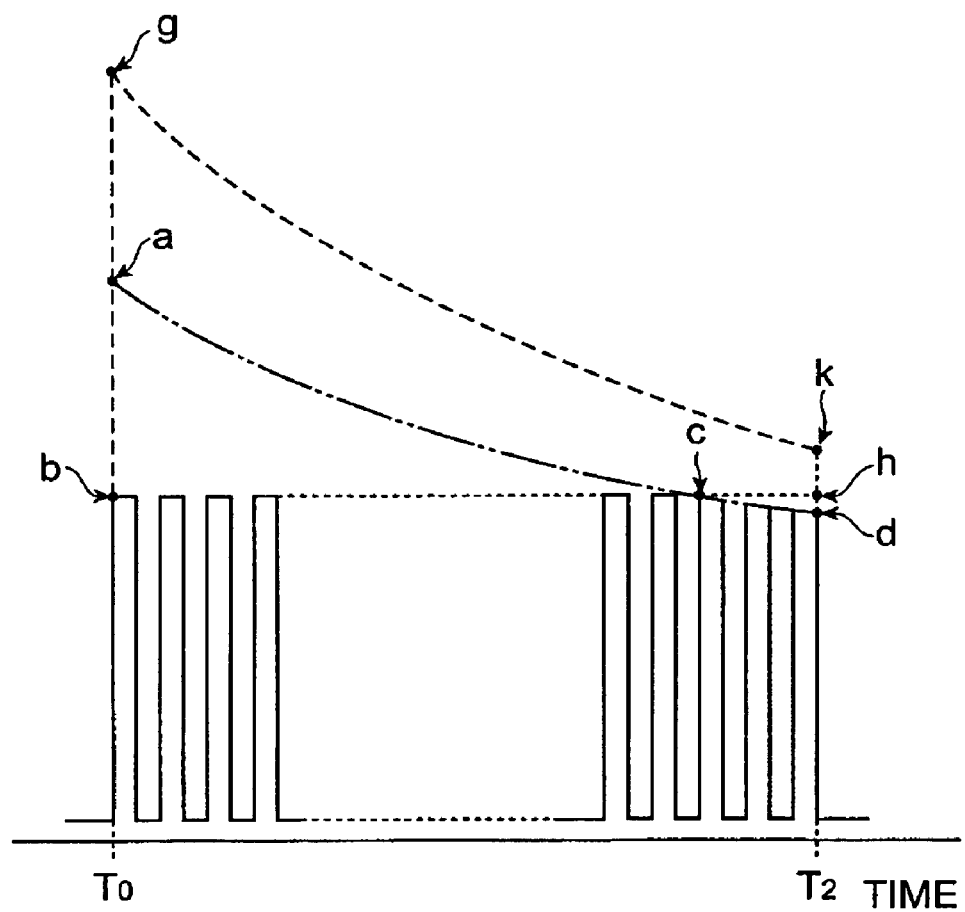

In FIG. 4, an envelope curve gk represents a voltage graph for an instantaneous permissible collector loss (described later) allowed for the current control device 34, given a desired device operation defined by the curve bcd. Therefore, if the actual capacitor voltage when the new values are entered is greater than the voltage at the point g, it is necessary to lower the capacitor voltage to the value at the point g. If the actual capacitor voltage is not greater than the voltage g, then there is no need to lower the capacitor voltage.

The second storage circuit 72 calculates a voltage value corresponding to the point g and outputs it as a digital signal. The voltage value at the point g is determined as follows. The charging voltage at the point a is determined based on the desired emission energy in the first storage circuit 62. Also, the pulse waveform, the number of pulses, the pulse width, and the pulse spacing are determined, and the time T1 (cf. FIG. 3) is calculated. Based on these values, the stress area defined by the points g, b, c, d, and k is calculated so as to be not greater than the permissible stress on the current control device 34 as determined by the data stored in the second storage circuit 72. This calculation provides the voltage value at the point g. Alternatively, one can use a current control device 34 with a large permissible stress and add a certain preset fixed voltage value to the voltage at the point a if there is a sufficiently large control margin. After the voltage value at the point g is determined as described above, this value is output as a digital signal to the second voltage setter 74.

The second voltage setter 74 generates a digital reference voltage value corresponding to the point g for a comparator operation, converts the digital reference voltage to an analog reference voltage signal, and holds the analog reference voltage signal. The second voltage setter 74 outputs the analog reference voltage signal to the error detection amplifier 78.

The second voltage detector (capacitor voltage detecting means) 76 performs broadband noise filtering on the capacitor voltage. The broadband noise filtering shields the circuit formed by the second voltage detector 76, the error detection amplifier 78, the switch 80, the load resistor 82, and the second voltage setter 74 from excessive noise that may be present in the equipment. The broadband noise filtering function causes a delay but does not affect the circuit operation.

The error detection amplifier 78 compares the capacitor voltage with the reference voltage corresponding to the point g. If the capacitor voltage is above the reference voltage, the switch 80 is activated to connect the load resistor 82 to the capacitor 28 to discharge the capacitor 28 to a voltage below the maximum safe capacitor voltage at the point g. In the present embodiment the capacitor voltage is lowered to the voltage at the point a defined by the new parameters. When the capacitor voltage reaches the desired level below the maximum safe capacitor voltage at the point g, the switch 80 is deactivated to disconnect the load resistor 82 from the capacitor 28.

The switch 80 receives a signal from the error detection amplifier 78 to discharge the capacitor 28. For a direct current discharge, a semiconductor relay is an excellent switch type.

During the capacitor discharge period through the load resistor 82, the switch 80 provides a control signal to the pulse enabling circuit 70 to prevent the discharge lamp 18 from emitting light, Consequently, the discharge lamp 18 emits no light even with if the button 22 is depressed. When the charging voltage becomes lower than the voltage at the point g, the control signal is deasserted, and the discharge lamp 18 becomes ready to emit light when the button 22 is depressed.

When the capacitor voltage is between the points g and a, it is often the case that one emission discharges the capacitor to a voltage below the point a, and the second and subsequent emissions occur in the course of a normal operation with the capacitor being charged to the voltage at the point a.

In the cosmetic treatment apparatus 10 of the present embodiment, as described above, the maximum safe capacitor voltage applied to the capacitor 28 is determined based on the emission parameters provided to the input circuit 58 and if the actual capacitor voltage is larger than this maximum safe capacitor voltage, the capacitor is discharged to a voltage below the maximum safe capacitor voltage; therefore, it is feasible to reduce the load on the current control device 34 and thereby prevent an early failure of the device. This circuitry is preferably implemented by a software programmable controller designed for the operation described above. Also, it is also possible to use a logic circuit including a CPU.

Now it will be described how one can select the current control device 34 taking into account the permissible stress and the maximum ratings.

The envelope curve gk in FIG. 4 represents the voltage curve for the maximum stress allowable for the current control device 34 in obtaining the desired voltage control bcd. When the capacitor voltage changes along the envelope curve gk, the current control device 34 always performs the constant current control operation throughout the irradiation period from the time T0 to the time T2, as indicated by the line bch.

The stress on the current control device 34 in this case can be determined by summing the product terms each of which is the product of: (i) the difference between the gk voltage and the voltage b, (ii) the current corresponding to the point b, and (iii) the pulse width.

Since the pulse width is short, the time that the current flows through the current control device 34 is very short. In general the maximum collector loss specified as the official maximum rating indicates the maximum collector loss in a continuous current flow, and thus is different from the instantaneous collector loss in the instantaneous current flow. This instantaneous collector loss depends on a particular use of the device. Therefore, the instantaneous collector loss was determined experimentally using an actual circuit and a breakdown tolerance was experimentally determined as an approximate value. It was confirmed that the sample IGBT device operated safely when the permissible stress was ten times the maximum official collector loss rating. Accordingly, the cosmetic treatment apparatus 10 in the present embodiment can use a device whose maximum official collector loss rating is one tenth of the actual maximum stress on the current control device 34. The device cost can therefore be reduced. It was also confirmed that the actual permissible stress in a parallel arrangement of two current control devices 34 was approximately double that for a single device. Therefore, it is possible to use a plurality of current control devices 34 in parallel.

The equipment should be protected against abnormal conditions such as a failure of the discharge lamp 18 or a short in an output load system. In the cosmetic treatment apparatus 10 of the present embodiment, this protection is provided as follows.

While the microcurrent from the microcurrent supply 42 is fed to the discharge lamp 18, a lower voltage is applied to the discharge lamp 18 than during the pulsed emission. That voltage is approximately one quarter of the voltage at the point b (FIG. 3).

If the discharge lamp 18 fails, there can be a short in the discharge load system. In this case, the lamp voltage applied to the discharge lamp 18 becomes abnormally low, and therefore the short in the discharge load system can be detected by detecting an abnormal drop of the lamp voltage.

The lamp voltage is provided through the trigger transformer 38 to the voltage comparison circuit 86. The reference voltage from the reference voltage generator 84 is also provided to the voltage comparator 86. If the lamp voltage is not less than the reference voltage, the voltage comparator 86 does not assert its output error detection signal since the lamp voltage is assumed to be normal. If the lamp voltage is lower than the reference voltage, the voltage comparison circuit 86 asserts the error detection signal to the error detection amplifier 54.

If the output current of the current control device 34 is about to become abnormally large, a circuit (not shown) in current detector 36 assumes there is an abnormal condition and asserts its error detection signal to the error detection amplifier 54. In the present embodiment, the current of about 400 A and above is determined as abnormal.

The error detection amplifier 54 computes a logical sum of the error detection signals from the voltage comparison circuit 86 and the current detector 36 and outputs the logical sum to the switch 52. When either one of the two error detection signals is asserted, the switch 52 disables the current control device 34. The equipment is thus protected from excessive current flow failures in case of the abnormal events such as a short in the discharge load system.

The discharge lamp 18 has a limited lifetime, and its current and emission characteristics gradually change over the lamp lifetime. Therefore, the discharge lamp 18 needs to be regularly replaced. Different discharge lamps may have different discharge characteristics, and when the same voltage is applied to the lamps without controlling the current, there may be variations in the lamp current to provide different the emission energies. Hence the heat energy can also vary. Therefore, if the same patient is treated both before and after a lamp replacement, the settings should be adapted to the change. This is cumbersome.

In the cosmetic treatment apparatus 10 of the present embodiment, therefore, since there is a strong correlation between the current flowing into the discharge lamp 18 and the emission energy, the emission control is effected via the current control. If there is no current control, the emission of the discharge lamp 18 will depend upon the lamp and the length of use, and the current amount will also vary. The constant current control can provide the preset current even to lamps with different characteristics. Therefore, the emission is less dependent on the particular lamp or the use history of the lamp, and the settings do not need to change when the lamp is replaced or when the lamp has been used for some time. Therefore, it becomes feasible to associate treatment settings with a patient.

The duration of the constant current control section (the period between T0 and T1 in FIG. 3) may vary depending on the lamp discharge characteristics due to the variations among discharge lamps 18 or the changes caused by the lamp use, but the resulting variations of the emission energy in one irradiation period are insignificant. The reason is that the current provided to the discharge lamps 18 is kept at the constant current control value, so the impact of the lamp variations is minimized.

Since the current in the constant current control section is independent of the discharge characteristics of the discharge lamp 18, the heat variations due to the lamp replacement are minimized. As a result, even if the same patient is treated both before and after the lamp replacement, the settings for the old lamp can be used for the new lamp. The heat amount in the end stage of the irradiation (from the time T1 to the time T2) may differ slightly depending upon the particular discharge lamp 18 or the use history of the lamp, but the end stage is much shorter than the constant current control section and thus the overall cosmetic treatment is not affected. Furthermore, since each one-pulse emission in the constant current control section is constant and the heat amount per pulse in the early part of the end stage is approximately the same as in the constant current control section, stable cosmetic treatment effects can be provided.

The trigger transformer 38 can be replaced with an amplifier (e.g. a series of CMOS inverters), or can be used in addition to such an amplifier, or can be omitted.

The invention is not limited to the embodiments described above, and many variations and modifications are possible, Such modifications are not to be considered as a departure from the spirit and scope of the present invention, and in particular all improvements obvious to those skilled in the art are to be included in the scope of claims which follow.

What is claimed is:

1. A cosmetic treatment apparatus comprising:
    a discharge lamp for generating light for a cosmetic treatment;
    a capacitor for providing an electric current for operating the discharge lamp;
    a circuit for operating the discharge lamp in response to the electric current provided by the capacitor; and
    a current controller for controlling the electric current flowing from the capacitor to the circuit, wherein the current controller is disposed between the capacitor and the discharge lamp,
    and further wherein the capacitor voltage decreases when the current flows from the capacitor to the circuit and the current controller is operative such that during at least a first part of the cosmetic treatment the current controller controls the current flowing to the circuit to be substantially constant, and during at least a second part of the cosmetic treatment the current controller controls the current flowing to the circuit to depend on the capacitor voltage.

2. The apparatus according to claim 1, wherein a light emission by the discharge lamp is a function of the current provided to the circuit.

3. The apparatus according to claim 2, wherein the light emission increases if the current provided to the circuit increases.

4. The apparatus according to claim 1 further comprising a pulse generator,
    wherein the current controller converts the electric current provided by the capacitor to a pulsed current in response to pulses from the pulse generator.

5. The apparatus according to claim 4, wherein the pulse generator generates a series of pulses of an identical pulse width.

6. The apparatus according to claim 1 further comprising:
    an input circuit for specifying a desired emission for the discharge lamp; and a charging voltage determining circuit for determining a charging voltage for the capacitor based on the emission specified by the input circuit.

7. The apparatus according to claim 6 further comprising:
a maximum safe capacitor voltage determining circuit for determining a maximum safe capacitor voltage based on the emission specified by the input circuit;
a capacitor voltage detecting circuit for detecting the capacitor voltage; and
a voltage reduction circuit coupled to the maximum safe capacitor voltage determining circuit and the capacitor voltage detecting circuit, for reducing the capacitor voltage when the capacitor voltage exceeds the maximum safe capacitor voltage.

8. The apparatus according to claim 1 further comprising a determining circuit for determining whether the lamp voltage is normal or abnormal,
wherein when the determining circuit determines that the lamp voltage is abnormal, the current controller is disabled from providing the current to the circuit.

9. The apparatus according to claim 1, wherein a second time period for the second part of the cosmetic treatment is less than or equal to 0.4 multiplied by the sum of a first time period for the first part of the cosmetic treatment and the second time period.

10. A cosmetic treatment method comprising:
converting a current flowing from the capacitor to a series of current pulses;
providing the current pulses to a circuit coupled to a discharge lamp which generates light for a cosmetic treatment, wherein a light emission of the discharge lamp depends on a current magnitude of the current pulses; and
wherein the cosmetic treatment comprises at least a first stage in which a plurality of said current pulses is generated, and during the first stage the capacitor voltage decreases but a maximum current of each pulse does not decrease.

11. The method according to claim 10, wherein during at least a second stage of the cosmetic treatment the maximum current of each pulse decreases with the capacitor voltage.

12. The method according to claim 10, wherein the light emission of the discharge lamp depends on the current provided to the circuit in such a way that the light emission increases with the current provided to the circuit.

13. The method according to claim 10, wherein the current pulses have an identical pulse width.

14. The method according to claim 10 further comprising:
receiving one or more parameters defining a desired emission for the discharge lamp; and
determining a charging voltage for the capacitor based on the one or more parameters.

15. The method according to claim 14 further comprising:
determining a maximum safe capacitor voltage based on the one or more parameters;
detecting the actual capacitor voltage; and
reducing the actual capacitor voltage when the detected capacitor voltage exceeds the maximum safe capacitor voltage.

16. The method according to claim 10 further comprising:
determining whether the lamp voltage is normal or abnormal; and
not providing the current pulses to the circuit when the lamp voltage is abnormal.

* * * * *